United States Patent
Luo et al.

(10) Patent No.: US 9,424,656 B2
(45) Date of Patent: Aug. 23, 2016

(54) COMPUTER VISION BASED METHOD AND SYSTEM FOR EVALUATING AND GRADING SURGICAL PROCEDURES

(71) Applicant: University of Rochester, Rochester, NY (US)

(72) Inventors: Jiebo Luo, Pittsford, NY (US); Junhuan Zhu, Rochester, NY (US); Yousuf Mohamed Khalifa, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/710,254

(22) Filed: May 12, 2015

(65) Prior Publication Data
US 2015/0320510 A1     Nov. 12, 2015

Related U.S. Application Data

(60) Provisional application No. 61/992,188, filed on May 12, 2014.

(51) Int. Cl.
*G06K 9/00*      (2006.01)
*G06T 7/20*      (2006.01)
(Continued)

(52) U.S. Cl.
CPC . *G06T 7/20* (2013.01); *A61B 19/50* (2013.01); *G06T 1/0007* (2013.01); *G06T 3/4084* (2013.01); *G06T 7/00* (2013.01); *G06T 7/0014* (2013.01); *G06T 7/0036* (2013.01); *G06T 7/0071* (2013.01); *G06T 7/0081* (2013.01); *G06T 7/0095* (2013.01); *G06T 7/2006* (2013.01); *A61F 9/007* (2013.01); *G06T 2207/10004* (2013.01); *G06T 2207/10016* (2013.01); *G06T 2207/10024* (2013.01); *G06T 2207/10028* (2013.01);
(Continued)

(58) Field of Classification Search
CPC ....... G06T 1/0007; G06T 3/4084; G06T 7/00; G06T 7/0014; G06T 2210/41; G06T 2207/10004; G06T 2207/10016; G06T 2207/10024; G06T 2207/10028; G06T 2207/20061; G06T 2207/20081; G06T 2207/20141; G06T 2207/30041; G06T 2207/30196; G06T 7/0036; G06T 7/0071; G06T 7/0081; G06T 7/0095; G06T 7/20; G06T 7/2006; A61F 9/007
See application file for complete search history.

(56) References Cited
PUBLICATIONS

Bhatia (Real-time Identification of operating room states from video, Journal proceeding of the 19th innovative Applications of AI conference. May 26, 2007, pp. 1761-1766).*

(Continued)

*Primary Examiner* — Amara Abdi
(74) *Attorney, Agent, or Firm* — Robert D. Gunderman, Jr.; Patent Technologies, LLC (57) ABSTRACT

To increase the timeliness, objectivity, and efficiency in evaluating surgical procedures such as those performed by ophthalmology residents' learning of cataract surgery, an automatic analysis system for surgeries such as cataract surgery is provided to assess performance, particularly in the capsulorrhexis step on the Kitaro simulator. Computer vision technologies are employed to measure performance of this critical step including duration, centrality, circularity, size, as well as motion stability during the capsulorrhexis procedure. Consequently, a grading mechanism is established based on either linear regression or non-linear classification via Support Vector Machine (SVM) of those computed measures. Comparisons of expert graders to the computer vision based approach have demonstrated the accuracy and consistency of the computerized technique.

20 Claims, 10 Drawing Sheets
(10 of 10 Drawing Sheet(s) Filed in Color)

(51) Int. Cl.
  *A61B 19/00* (2006.01)
  *G06T 1/00* (2006.01)
  *G06T 3/40* (2006.01)
  *G06T 7/00* (2006.01)
  *A61F 9/007* (2006.01)

(52) U.S. Cl.
  CPC ............ *G06T 2207/20061* (2013.01); *G06T 2207/20081* (2013.01); *G06T 2207/20141* (2013.01); *G06T 2207/30041* (2013.01); *G06T 2207/30196* (2013.01); *G06T 2210/41* (2013.01)

(56) References Cited

PUBLICATIONS

Lalys et al ("A framework for the recognition of high-level surgical tasks from video images for cataract surgeries", IEEE, Feb. 13, 2012).*

Lalys et al. A framework for the recognition of high-level surgical tasks from video images for cataract surgeries. Journal. IEEE Trans Biomed Eng. Feb. 13, 2012. pp. 966-976. 59 (4). IEEE. Country not specified.

Blum et al. Modeling and Segmentation of Surgical Workflow from Laparoscopic Video. Journal. May 25, 2010. pp. 1-8. Publisher and country not specified.

Bhatia et al. Real-Time Identification of Operating Room State from Video. Journal. Proceedings of the 19th Innovative Applications of AI Conference. May 26, 2007. pp. 1761-1766.

Ballard. Generalizing the Hough Transform to Detect Arbitrary Shapes. Journal. Pattern Recognition. Sep. 23, 1980. pp. 111-122. vol. 13, No. 2. Pergamon Press Ltd. GB.

Padoy et al. On-line Recognition of Surgical Activity for Monitoring in the Operating Room. Journal. Association for the Advancement of Artificial Intelligence. Mar. 26, 2008. pp. 1-7. Publisher and country not specified.

Suzuki et al. Skill Evaluation from Observation of Discrete Hand Movements during Console Operation. Journal. Journal of Robotics. Feb. 15, 2010. pp. 1-13. Hindawi Publishing Corporation. Country not specified.

Bertalmio et al. Image Inpainting. Journal. Apr. 12, 2000. pp. 1-8. Publisher and Country not specified.

Barron et al. Performance of Optical Flow Techniques. Journal. Nov. 28, 2003. pp. 1-60. Publisher and Country not specified.

Ahmidi et al. Surgical Task and Skill Classification from Eye Tracking and Tool Motion in Minimally Invasive Surgery. Journal. Aug. 5, 2010. pp. 295-302. MICCAI 2010. Country not specified.

* cited by examiner

COMPUTER VISION BASED METHOD AND SYSTEM FOR EVALUATING AND GRADING SURGICAL PROCEDURES

CROSS REFERENCE TO RELATED PATENT APPLICATIONS

This application claims priority to U.S. Patent Application Ser. No. 61/992,188 filed May 12, 2014 entitled "Computer Vision Based Method And System For Evaluating And Grading Surgical Procedures" by Luo et al., the entire disclosure of which is incorporated herein by reference.

BACKGROUND OF THE INVENTION

1. Field of the Invention

The present invention relates generally to the field of digital image processing and, more particularly, to a computer vision based method and system for evaluating and grading surgical procedures.

2. Description of the Related Art

The Accreditation Council for Graduate Medical Education (ACGME) requires that each ophthalmology residency training program provides a wet laboratory for residents to prepare intraocular surgery prior to live human surgery. Training residents in cataract surgery has been a challenge for residency programs as a result of several factors:
1. Surgery is usually performed on an awake patient.
2. Wet lab facilities are underfunded.
3. Faculties are not funded for teaching.
4. Lack of high-fidelity, low-cost simulation models.

Porcine eyes were the traditional model for cataract surgery, but because of differences in anatomy and tissue consistency, teaching cataract surgery on a porcine eye can lead to a resident learning poor technique in performing capsulorrhexis and in phacoemulsification. Recently, the Kitaro simulation device was introduced, which provides a relatively low-cost, high-fidelity teaching tool.

We have recently incorporated the Kitaro system in a six-week course at the Flaum Eye Institute. University of Rochester Medical Center to help transition residents to the operating room. The Kitaro system consists of a synthetic cornea and cataract that mimics the anatomy and spatial relationships of a human eye. Trainees can practice all steps of cataract surgery using this system. Cataract surgery consists of seven surgical stages: 1) incisions, 2) capsulorrhexis, 3) hydrodissection, 4) phacoemulsification, 5) cortical clean-up, 6) lens insertion and 7) closing. Capsulorrhexis is the step in which a round, concentric, and symmetric hole is fashioned in the anterior capsule of the cataract using a bent needle and forceps. In week two of the Flaum Cataract Curriculum at the University of Rochester Medical Center, capsulorrhexis is taught in a didactic session with surgical video examples. The residents are then given a homework assignment to digitally record their practice sessions and submit for grading. The process of manually grading wet lab videos is time consuming for faculty and delays feedback to the trainee; additionally, the objectivity of faculty grading is not established.

Computer vision is a technology applied to analyze images, videos, and high-dimensional data from the real world in order to automate analysis and objectively assess. Computer vision technology, as well as image processing, is widely utilized in medical fields, such as in tumor detection and vessel analysis. For surgical training, especially for training through multimedia, computer vision technology can play an important role in analysis and evaluation of recorded practice sessions in a real-time, objective fashion.

What is needed is a system and method to increase the efficiency and speed of the surgical technique evaluation process.

It is thus an object of the present invention to provide a computer based evaluation system for cataract surgical techniques. It is another object of the present invention to provide a computer based evaluation system for cataract surgery videos. It is another object of the present invention to provide a computer based evaluation system for cataract surgery that recognizes the details in each of the surgical stages of cataract surgery. It is yet another object of the present invention to provide a computer based evaluation system for evaluating and grading cataract surgical techniques.

BRIEF SUMMARY OF THE INVENTION

In accordance with the present invention, there is provided a computer vision based method and system for evaluating and grading surgical procedures where computer vision techniques are used to obtain segmented key frames and optical flow magnitude curves for each surgery procedure; and duration, spatiality, and motion features are computed and applied in linear regression and Support Vector Machine (SVM) models to assign grades.

The foregoing paragraph has been provided by way of introduction, and is not intended to limit the scope of the invention as described by this specification, claims and the attached drawings.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

DESCRIPTION OF THE PREFERRED EMBODIMENTS

The present invention is applicable to evaluating, and in some embodiments grading, surgical procedures in general. Cataract surgery is provided herein as an example, and not a limitation, of the present invention and the various embodiments described and envisioned herein.

A cataract surgery video evaluation system for capsulorrhexis procedures comprises three aspects: duration, spatiality, and motion.

First, computer vision techniques are used to obtain segmented key frames and optical flow magnitude curves for each surgery procedure. Next, the duration, spatiality, and motion features are computed and applied in linear regression and Support Vector Machine (SVM) models to assign grades. Experimental results reveal that our grading system can achieve reasonable agreement with the experts. Moreover, our experimental results also establish the consistency of the automated grading system with respect to the subjectivity of human raters. The application of computer vision in surgical simulation training and in real surgical video assessments is expected to play an increasingly critical role in the competency-based paradigm adopted by accrediting institutions.

Figure 1:
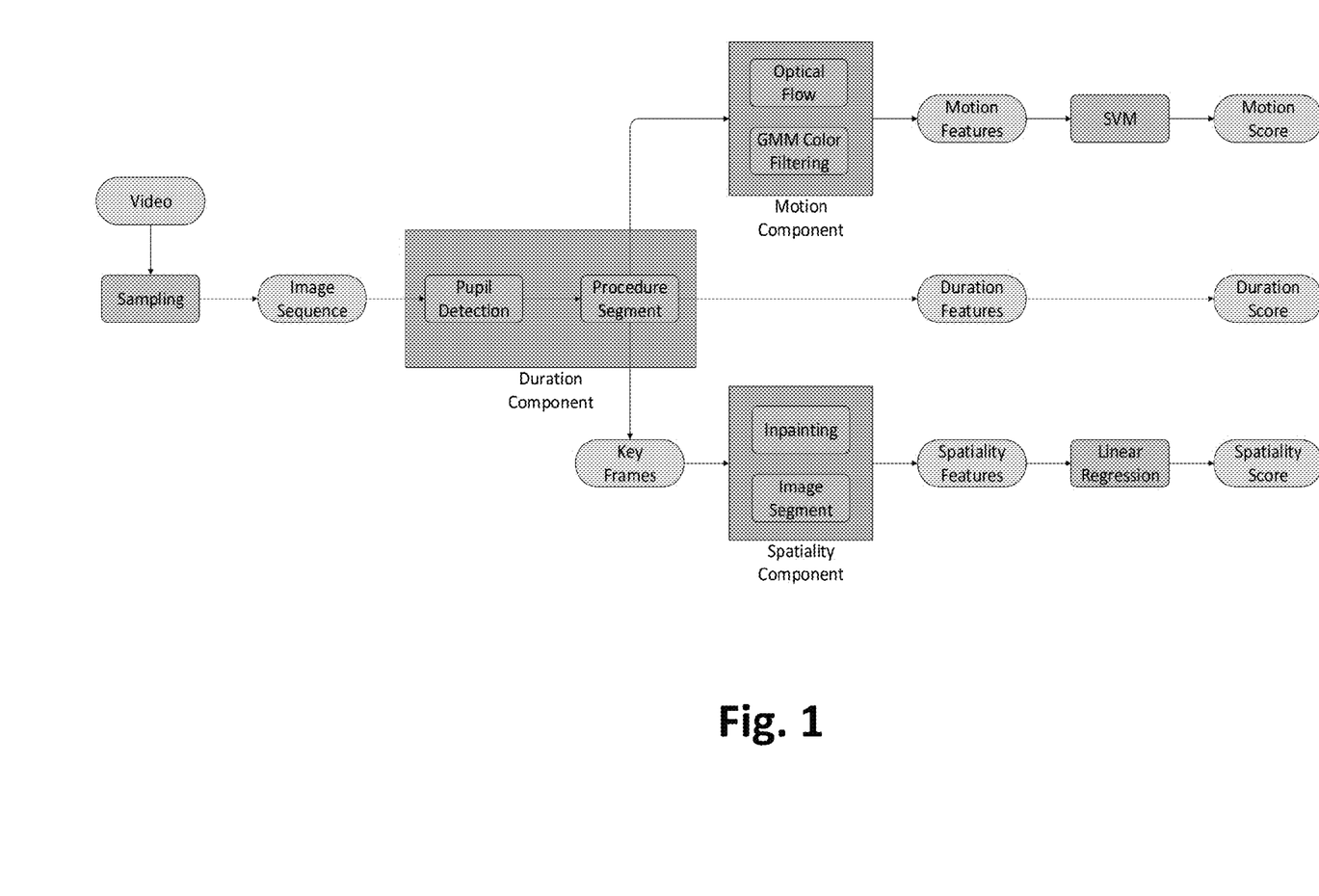
FIG. 1 is a flowchart depicting a method of the present invention.

FIG. 1 depicts the framework of the cataract surgery video evaluation system for simulated capsulorrhexis procedures. As shown in FIG. 1, a video is represented by a sequence of images through sampling. Next, pupil detection is applied to obtain the Region of Interest (ROI). Since a video may contain multiple independent capsulorrhexis procedures, procedure segmentation is performed based on the ROI's location changes to obtain the duration features. The completion of capsulorrhexis is identified as the key frame for each procedure. By processing the key frames through inpainting and image segmentation, spatiality features including size, centrality and circularity can be extracted. Next, optical flow for each independent capsulorrhexis procedure is calculated, and the average motion changes are measured to represent the proficiency and stability of the operations, which is utilized as motion features. Gaussian Mixture Model (GMM) color filtering is leveraged to remove spurious optical flow values caused by membrane changes. After obtaining all the features of the three aspects, we use either linear regression or the Support Vector Machine (SVM) to train the model for score assignment. Experiments on 50 independent capsulorrhexis procedures were done and the results support the accuracy and consistency of our system.

This work is closely related to 1) surgical video processing, 2) surgical stage recognition, and 3) video based rating. Among the various applications of surgical video processing, stage recognition and rating are the focus of our work.

Figure 2:
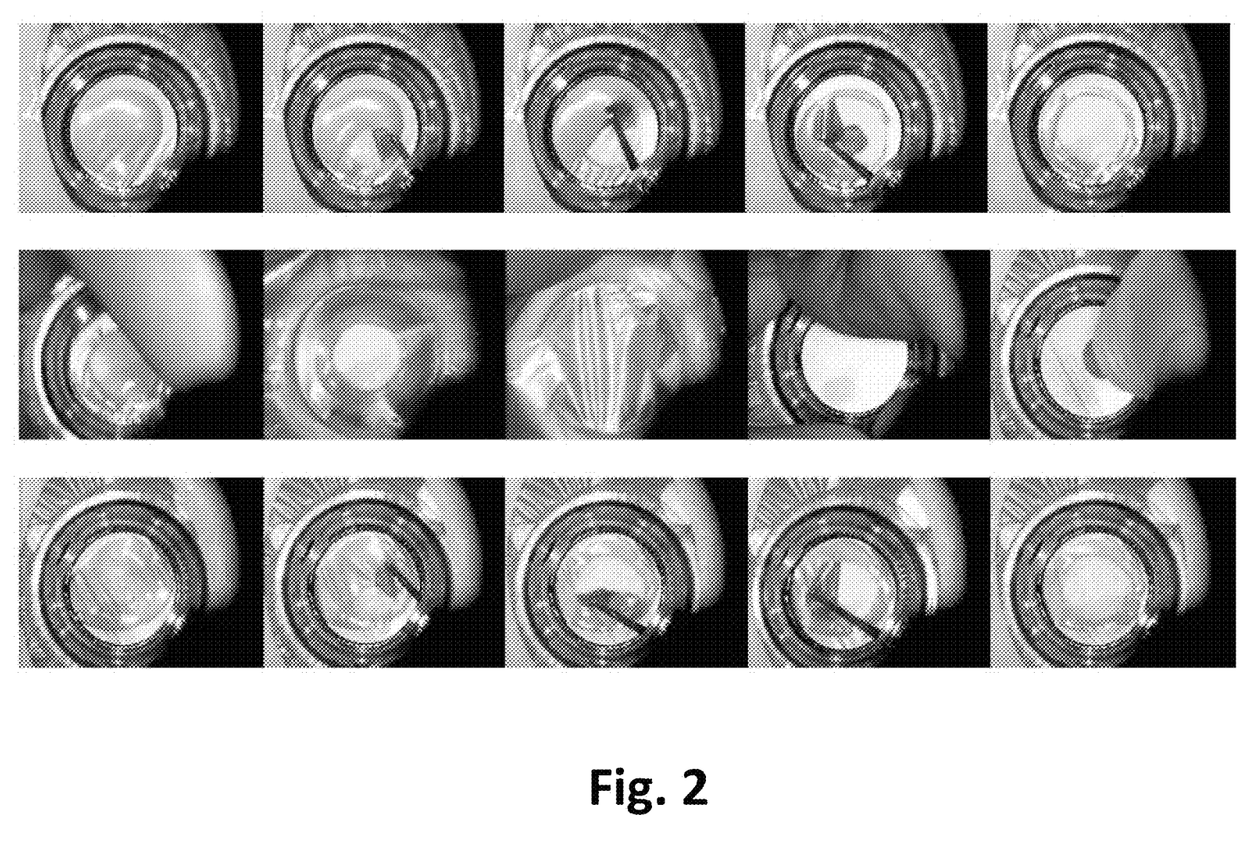
FIG. 2 depicts independent capsulorrhexis procedures in rows 1 and 3 with preparation work in row 2.

Time duration of a cataract surgery is considered important for performance evaluation. In general, surgeries that take less time are preferred by both patients and ophthalmologists. It is intuitive that experienced ophthalmologists always complete a cataract surgery faster than novices in this field, because they have performed the surgeries numerous times and are very familiar with the details in the surgery. Therefore, we first assign the duration score to the capsulorrhexis videos in terms of the video lengths. For videos recording only one capsulorrhexis procedure, the video length can be obtained directly. However, a person may perform capsulorrhexis surgery again and again, and record them into one video. In such cases, a video may contain multiple capsulorrhexis procedures as the ophthalmological trainee or other medical person or personnel practiced the capsulorrhexis procedure repeatedly. Because those capsulorrhexis procedures are assumed independent, the evaluation should be applied to each of them separately and this requires the segmentation of the video. As shown in FIG. 2, independent capsulorrhexis procedures are separated by preparation work in between. The preparation work also takes time but these time durations should not be counted in the duration score. To separate the independent capsulorrhexis procedures from videos and discard the preparation work part, we segment the videos and obtain the duration score for each capsulorrhexis procedure. More details are described in the following.

In FIG. 2, the first row and third row are independent capsulorrhexis procedures in one video. The second row is the preparation work between them.

Pupil Detection

Because the vital operation of capsulorrhexis is using a thin needle to tear a concentric and symmetric hole inside the pupil, most surgical actions are performed within the pupil area and the information outside this area is non-informative and irrelevant for evaluation.

To increase the efficiency of the computerized evaluation system, it is intuitive to only concentrate on the area where the capsulorrhexis actions may take place. For each video frame, we should first locate the position and determine the size of the pupil area, which is called the Region of Interest (ROI). This region is always circular, which motivates us to apply the circular Hough transform to detect the pupil boundaries.

Figure 3:
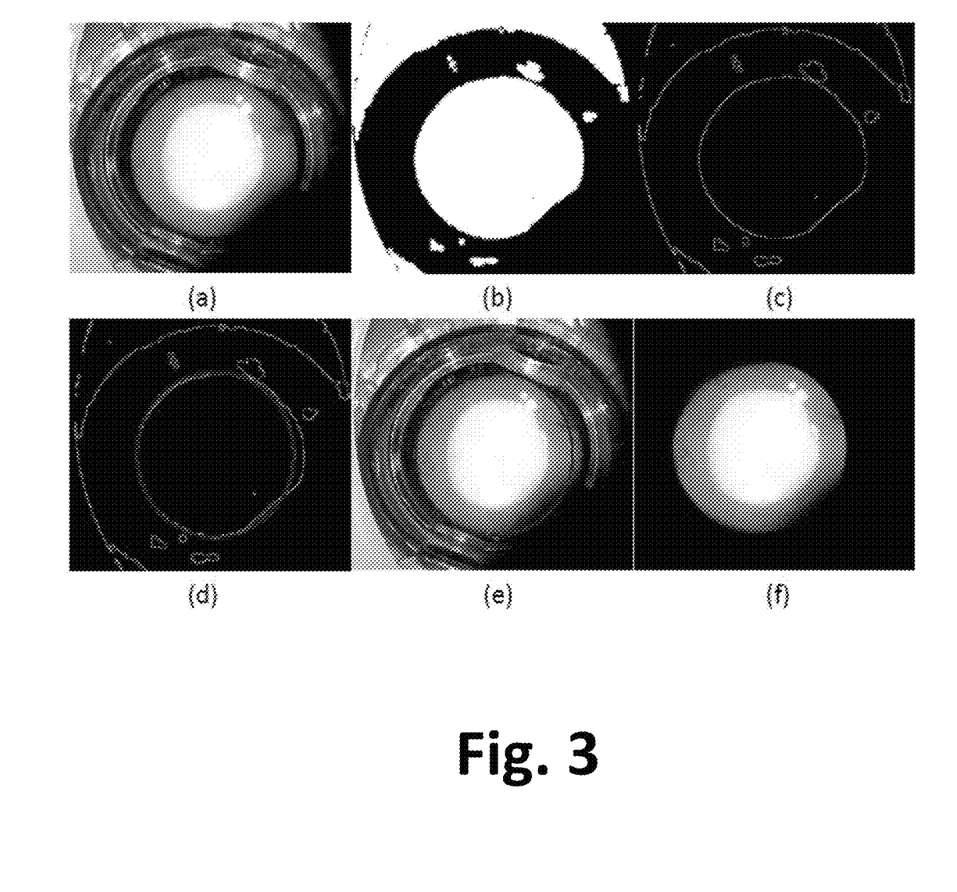
FIG. 3 depicts various steps of pupil detection.

FIG. 3 depicts different steps of pupil detection, (a) original image, (b) segmentation image, (c) edge image, (d)(e) detected circles and (f) masked image (ROI image).

First, note that all the rings used to indicate the pupil are in black or gray color (may contain light reflections), we compute the binary image for each frame using a thresholding method by representing all black or gray pixels as black and others as white. To avoid the interference of the textures caused by reflections on the black rings, a morphological opening operation is performed to remove overly thin patterns and obtain more compact results, as shown in FIG. 3 (b). Next, we apply the Canny edge detector to the binary images to obtain an edge image as shown in FIG. 3 (c), which is much more clear than detecting edges directly on the gray-scale images. Since noise reduction and non-maximum suppression have been leveraged in the Canny edge detector to improve the performance, no other pre-processing work is applied in this study.

Next, we apply the circular Hough transform to detect the circular elements in the edge images. The Hough Transform has been widely utilized in digital image processing and computer vision to detect parameterized shapes. According to the shape to be detected, a parameter space is generated first. To find the local maxima cells which have high possibilities of being the proposed shape, a voting procedure is applied to the parameter space. The target shapes can be detected by transforming the local maxima cells to the original space. For the circular Hough transform, a circle in a plane coordinate system $I(i, j)$ is defined as below:

$$(i-a)^2 + (j-b)^2 = r^2 \qquad (1)$$

In the above equation, $(a, b)$ is the coordinate of the circle's center and r is the radius of the circle. By defining the parameter space as $P(a, b)$, each edge point in $I(i, j)$ is a circle in $P(a, b)$ given a predefined radius r. Next, we increment all cells in the parameter space $P(a, b)$ satisfying Equation (1) and search for the local maxima cells with the greatest value in their neighborhood. Finally the position of the circles we are trying to detect can be located according to these local maxima cells, as shown in FIGS. 3 (d) and (e), where the blue circles are detected pupil boundaries. The area inside the pupil is the ROI and all the information outside the ROI is discarded to increase the efficiency, as shown in FIG. 3 (f). Note that there are always two circles detected, and we choose the inner circle as the pupil boundary in this case.

Procedure Segmentation

Figure 4:
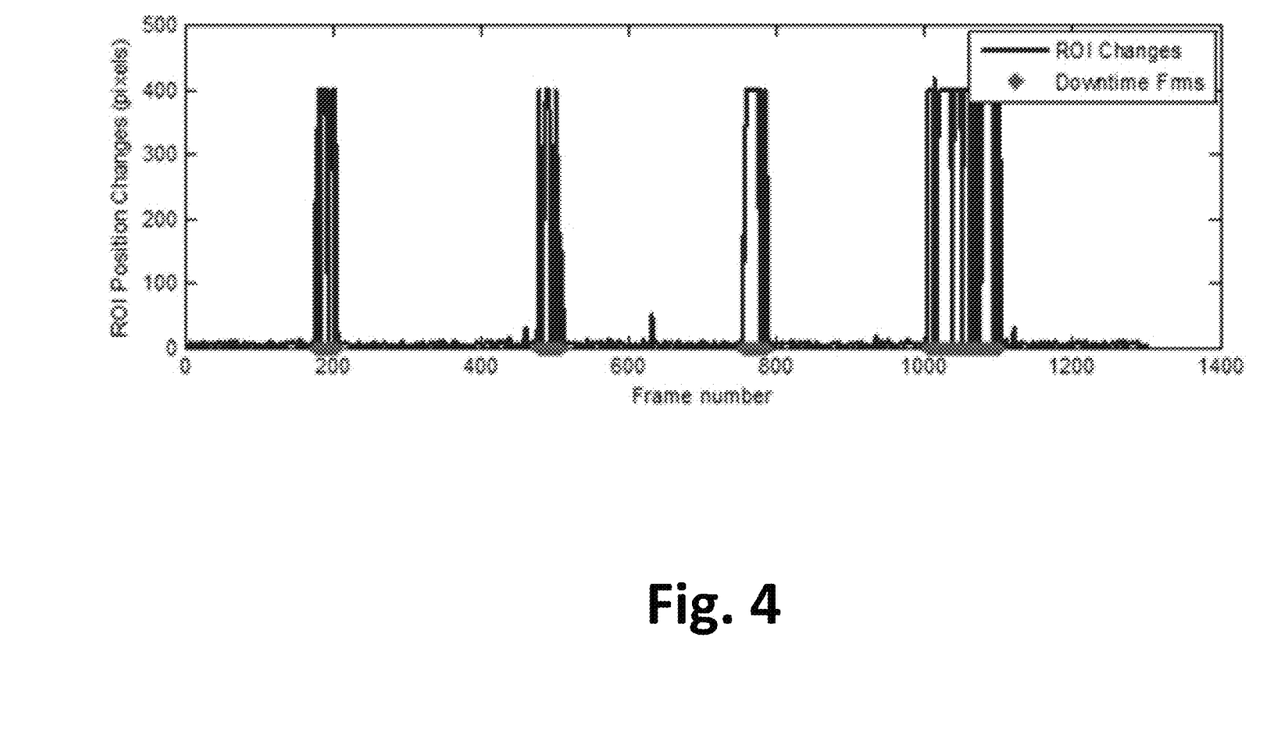
FIG. 4 depicts examples of action frame and key frame detection.

For videos containing multiple capsulorrhexis procedures, we classify the video frames into two types: action frames and downtime frames. Frames indicating the surgical actions are defined as action frames. Independent capsulorrhexis procedures are represented by several sets of consecutive action frames. To separate action frames, frames indicating the preparation work are defined as downtime frames. In addition, key frames are defined as the last frame of an independent capsulorrhexis procedure where all surgical actions have been completed. To identify action frames, downtime frames, and key frames, we track the ROI position over the image sequence. To recognize the starting of a capsulorrhexis procedure, as shown in FIG. 4, we find the start point of a long enough period which contains no obvious ROI position changes. Furthermore, we regard the frame prior to a set of obvious ROI position changes as the key frame, which also indicates the end of a capsulorrhexis procedure (a consecutive action frame set). The remaining frames, defined as downtime frames, belong to the period of preparation and should not be used for surgery evaluation.

Duration Score

According to the starting frame and the key frame (ending frame) of each capsulorrhexis procedure, we obtain the time duration of the actual surgery performing period. The duration score is simply represented by seconds of the time duration. Higher duration score indicates worse performance on duration. An average duration score is computed from the training data for comparison. Medical personnel such as experienced ophthalmologists should take less time on performing one capsulorrhexis procedure than ophthalmological trainees.

Spatiality Measure

The essential step of capsulorrhexis is using a bent needle and forceps to fashion a round, concentric, and symmetric hole in the anterior capsule of the cataract. The spatial features of the hole should be an important factor for evaluation. Note that the hole is required to be concentric and symmetric, therefore centrality and circularity are regarded as two aspects of the spatial features. In addition, size is another aspect influencing the performance. The hole should be as large as needed while the boundary of the hole is not allowed to touch the pupil's boundary. Consequently, we propose to measure the hole's size, circularity and centrality. Because key frames with completed holes have been obtained, the spatiality measure is only applied to key frames instead of the entire image sequence.

Reflection Removal

When recording the capsulorrhexis practicing procedures, the lights are sometimes reflected in the pupil area or ROI, which may confuse the subsequent analysis. Without any pre-processing, it is very difficult for the computer and related program to determine the original color (or colors) of a light spot. However, this kind of distortion can be repaired by a computer vision technology called inpainting. In most cases, the color of the light spots is pure bright white, thus the default definition of the reflections are pixels with colors close to pure bright white. To prevent mixing the light spots with other useful regions, the color of light spots should be identical. If the reflections are not white or the peeled region is similar to the reflections, our system allows the user to indicate this situation and ignore the reflection removal procedure.

Figure 5:
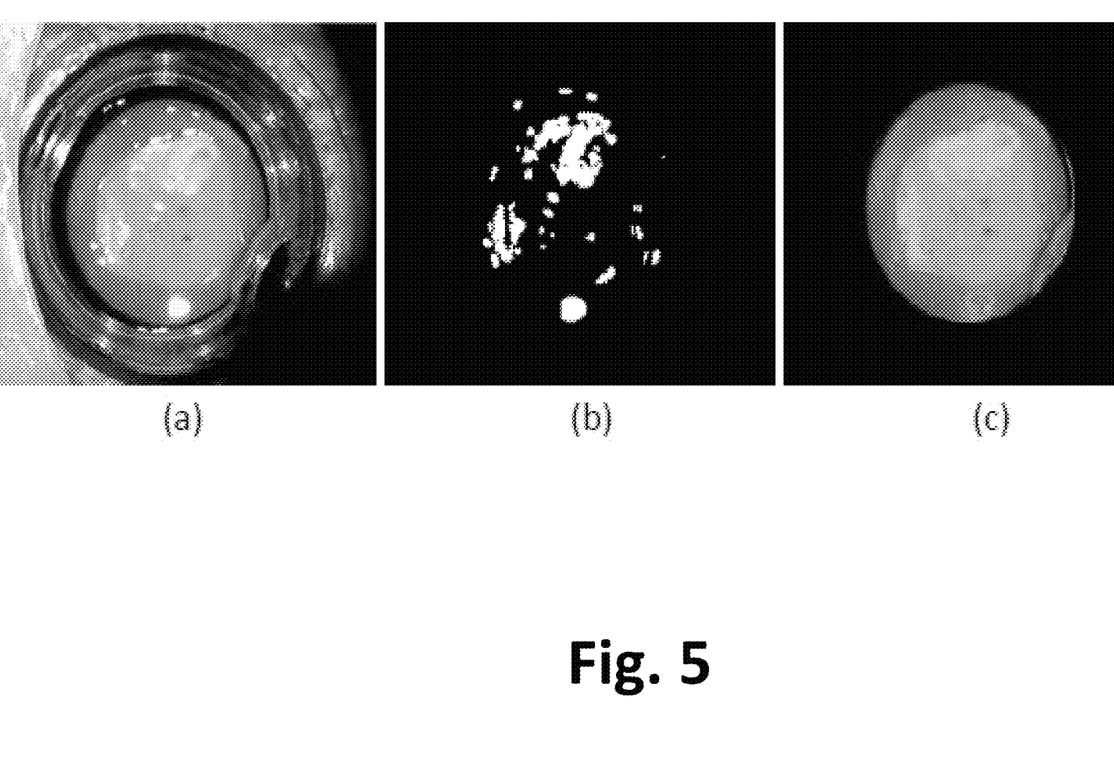
FIG. 5 depicts examples of the applications of inpainting with (a) original image, (b) label image and (c) restored image.

For an image frame where the light reflections and the peeled region are similar such as FIG. 5 (a), we first compute the regions needed to be filled-in. In this study, we simply choose pixels having color similar to pure bright white, and obtain a label image as shown in FIG. 5 (b), where the white regions indicate the region to be inpainted. Next, the inpainting algorithm is applied to those regions and results in the image with reflection removed, as shown in FIG. 5 (c). Compared with the original image, the processed image has more clear boundaries of the peeled regions, which benefits from the following procedure of image segmentation.

Image Segmentation

In the ROI of each frame, there are mainly three kinds of regions: 1) the membrane region, indicating the lens membrane to be peeled. 2) the peeled region, where the peeling actions are taken. 3) the tool region, representing the surgical tool used to perform the peeling actions. The distribution of these three kinds of areas plays a vital role in describing the surgical procedures and evaluating the surgical performance, especially the shape of the peeled area.

In our system, k-means clustering is applied to obtain this distribution. There should be some relatively clear dissimilarity between different areas. In one example, we set k=3, representing the membrane regions, the peeled regions, and the black color regions, which can be either the ring or the tool. The initialization procedure is very important for k-means clustering. To increase both the efficiency and accuracy of the segmentation results, we choose the initialization strategies as follows.

1. For the membrane region cluster, we initialize the 1st centroid as the average value of all the pixels along the circle path whose radius is 4/5 of the ROI's radius.

2. For the peeled region cluster, we initialize the 2nd centroid as the average value of all the pixels within the circle path whose radius is 1/5 of the ROI's radius.

3. For the black color region cluster, we initialize the 3rd centroid as the darkest pixel, in other words, the pixel having the lowest value in corresponding gray-scale image within the ROI.

Figure 6:
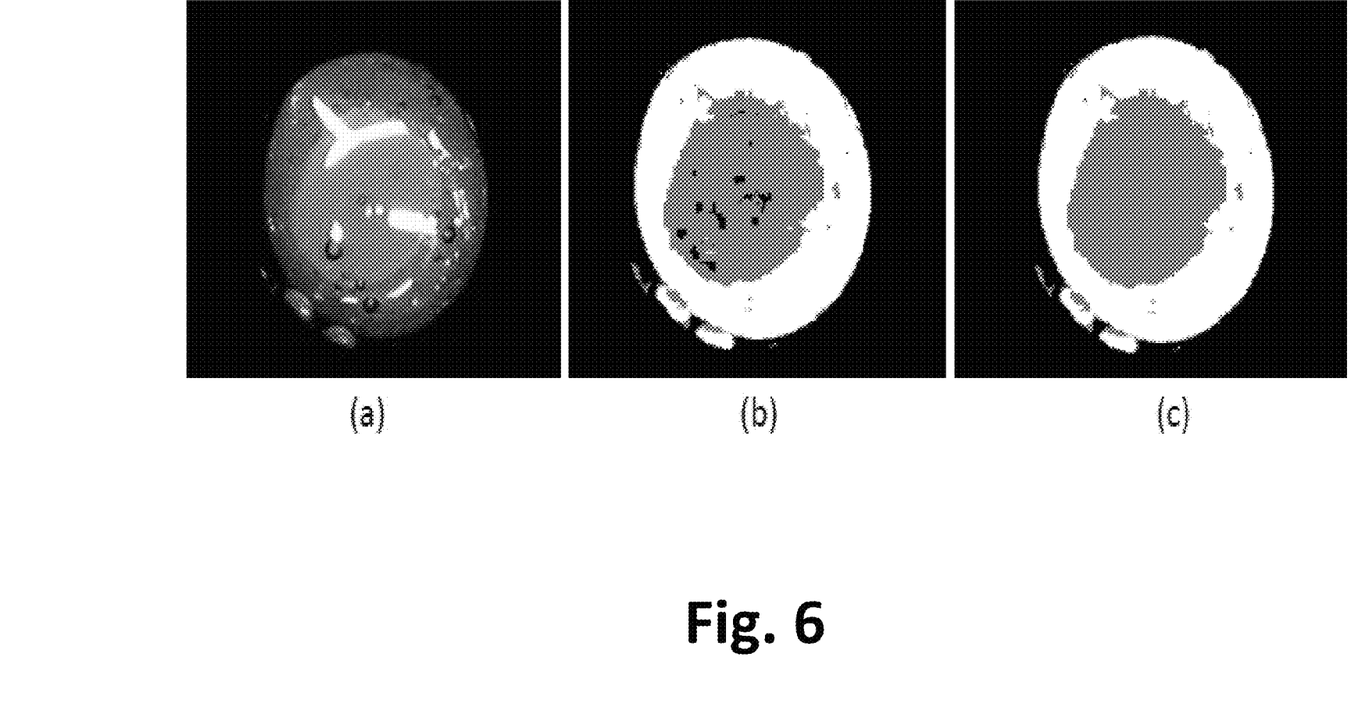
FIG. 6 are examples of image segmentation via k-means clustering to determine the capsulorrhexis area (white areas)

After k-means clustering, pixels are separated into three categories, as shown in FIG. 6 (b). However, due to the imaging distortions, the shape of the peeled region may not reflect the real situations. Thus we need to apply several image processing technologies to refine the segmentation results. First, in order to determine which cluster represents the peeled regions, we check all the pixels within the circle whose radius is 1/8 of the ROI's radius. The label with the largest number of pixels within this circle indicates the peeled region cluster. Next, we fill in the holes within the largest peeled region, as shown in FIG. 6 (c). Then we remove the isolated peeled regions which are not connected with the main peeled region, and obtain the image. To make the main peeled region's boundary smoother and more similar with the real case, we apply morphological opening operation to remove unwanted prominent components. Finally, to address the problem of gaps along the boundary, convex hull are applied to fill in those notches.

Spatiality Score

Figure 7:
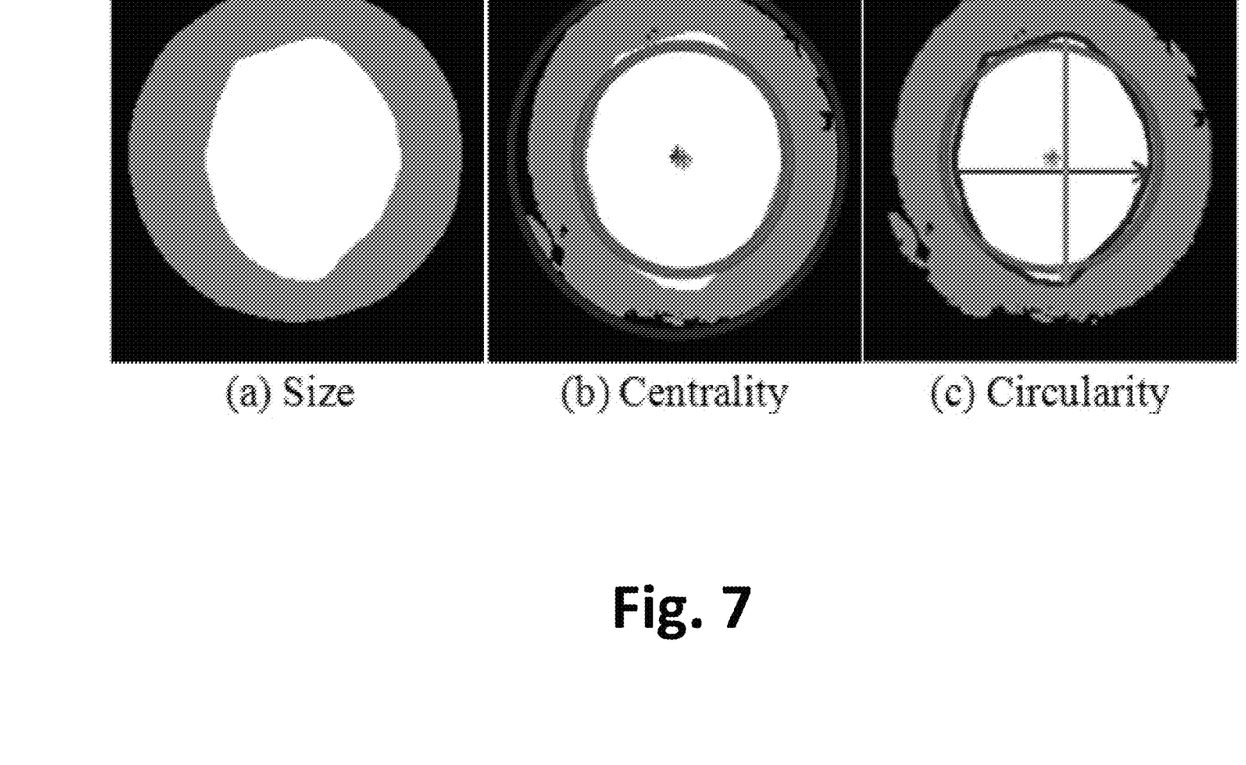
FIG. 7 depicts three measurement factors of spatial aspects: (a) size, (b) centrality and (c) circularity.

The spatial appearance of capsulorrhexis areas (peeling areas) in the key frames is very useful for determining the quality of the surgical performance. To evaluate the appearance of the peeling areas, we propose to use three spatiality factors: size, centrality and circularity. For each key frame, a grade between 0 and 2 will be assigned on each spatiality factor indicating poor, fair, and good. The grading mechanism is based on the linear regression of one or more sub-factors. As shown in FIG. 7 (a), for size, we use the ratio of the capsulorrhexis area (white area) and the pupil area (the gray area pluses the white area) to represent the performance. In addition, centrality is indicated by the position changes between the center of the pupil (blue dot) and the center of the capsulorrhexis area, as shown in FIG. 7 (b). Circularity is more complicated than the previous two factors, which is represented by three sub-factors: (c1) The ratio of the largest horizontal length (pupil line) and the largest vertical length (green line); (c2) The ratio of the perimeter's (blue boundary) square and the area of the capsulorrhexis part (white area); (c3) The variance of the distances between the perimeter pixels (blue boundary) and the center of the capsulorrhexis part (red dots). We denote the score of each sub-factor as y and the features of each sub-factor as X. After normalization on X, the spatiality score is calculated using linear regression.

$$y = w^T X + b \qquad (2)$$

In Equation 2, w represents the weights of sub-factors and b is a constant. Size, as well as centrality, has only one sub-factor. Circularity has three sub-factors, and normalization is applied to X during calculation. According to the values of y, three sub-factors scores are assigned to each key frame.

Motion Measure

Motion is another important aspect regarding a resident's performance in a cataract surgery. In general, an ophthalmological resident is supposed to perform steadily throughout the capsulorrhexis procedure. Stable motions always result in more smooth peeled area. On the contrary, if the surgeon's hand shakes significantly, the boundary of the peeled may contain serrated patterns and decrease the circularity. Moreover, less proficient residents tend to have useless motions, which may also lead to longer operation time, or duration aspect. Therefore, in this study we use the stability of motions to evaluate the performance of a capsulorrhexis procedure from the motion aspect.

Optical Flow

We apply optical flow to compute the motion of each capsulorrhexis procedure. Optical flow is the pattern of apparent motion of objects, surfaces, and edges in a visual scene caused by the relative motion between an observer and the scene, as shown in the first column and third columns in FIG. 9. The average motion changes are calculated to represent the smoothness.

Color Filtering

Figure 8:
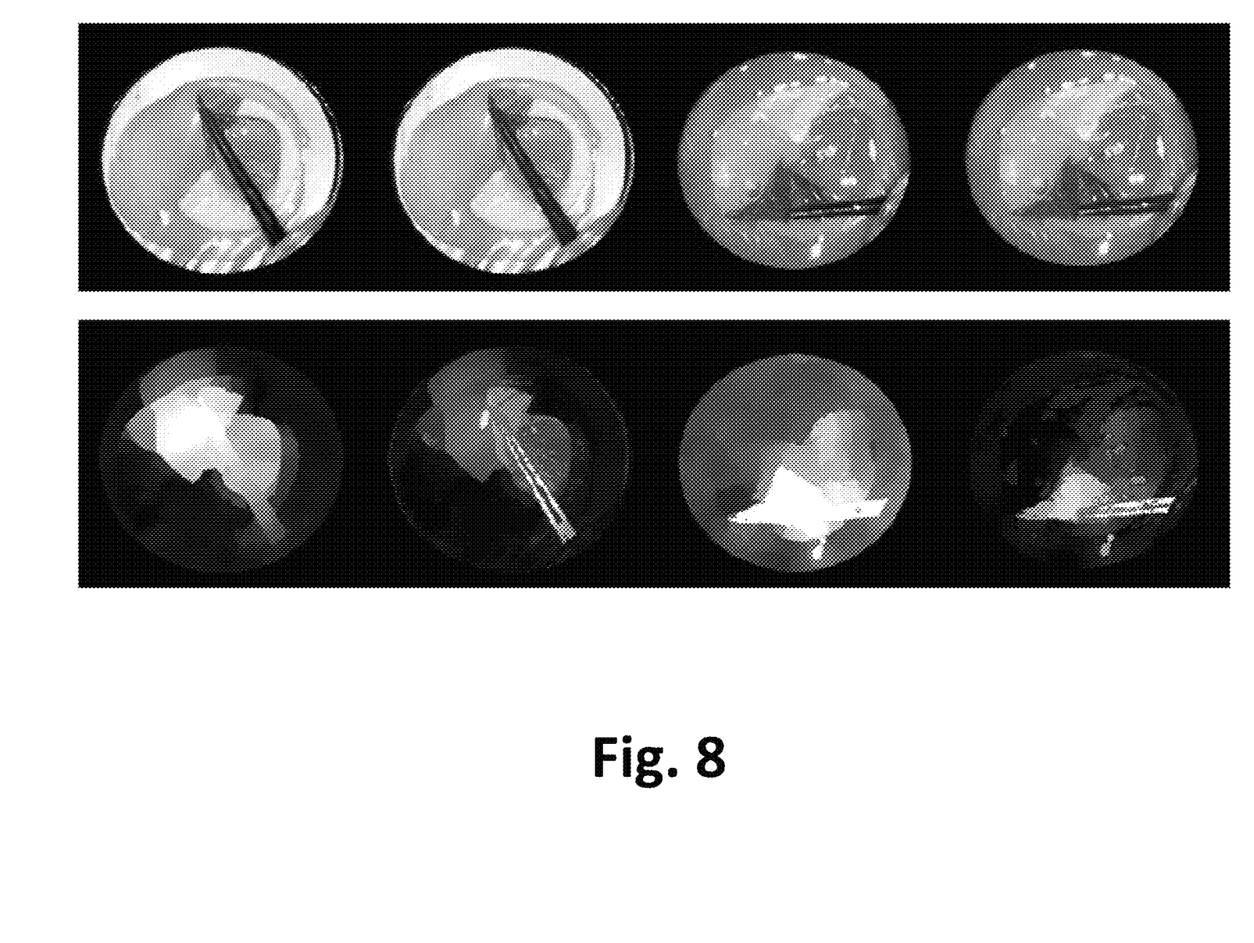
FIG. 8 depicts original images in the first and third columns and Gaussian Mixture Model color filtering images in the second and fourth columns.

In evaluating motion stability, we concentrate on the surgical tool's motion. However, as the ophthalmologist peels on the membrane, part of the membrane is removed and causes the optical flow, as shown in the first and third columns in FIG. 9. This kind of motion makes the optical flow map noisy. To increase the accuracy, we apply the Gaussian Mixture Model (GMM) to identify the effective motion regions. We assume that all the key frames contain no surgical tool since the surgical procedure is completed at that point, as shown in FIG. 8 (a). Because the pixel values within the pupil are supposed to satisfy the Gaussian mixture distribution, as shown in FIG. 8 (b), we can compute the center and variance of each Gaussian mixture distribution for the key frames. FIG. 8 (c) shows the two GMM centers of the colors in (a). According to the derived GMM, we apply color filtering to the action frames. If the pixel values in a frame are close to the GMM centers, we reduce the motion in this pixel. On the other hand, if the pixel values are far different from the GMM centers, we maintain the motion magnitude. All pixels retaining the original motion magnitude are defined as the effective motion region, as shown in the blue cast region in the second and forth columns in FIG. 9. The corresponding images are the filtered optical flow magnitude images, where the noise is removed and the tool's motion is preserved.

Figure 9:
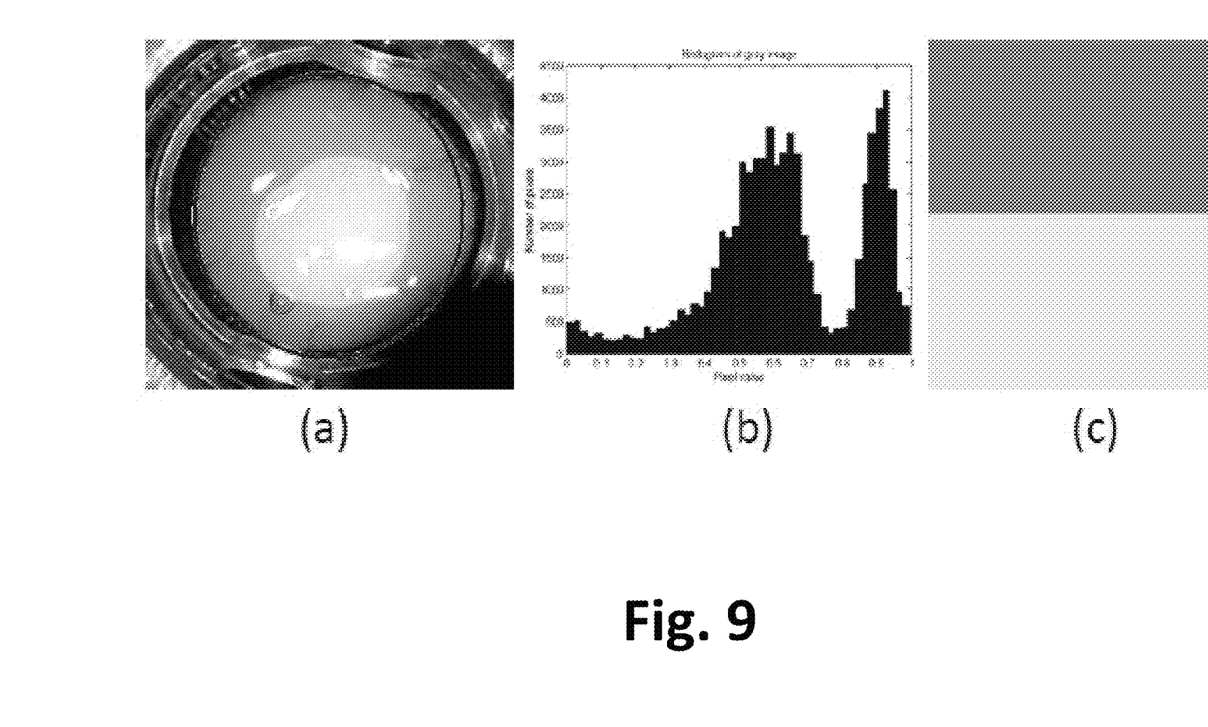
FIG. 9 depicts a Gaussian Mixture Model for color filtering.

FIG. 9 shows where the first and third columns are original images and corresponding optical flows. The second and forth columns are images with GMM color filtering and filtered optical flows. Blue-cast regions are far from the GMM centers.

Motion Score

Figure 10:
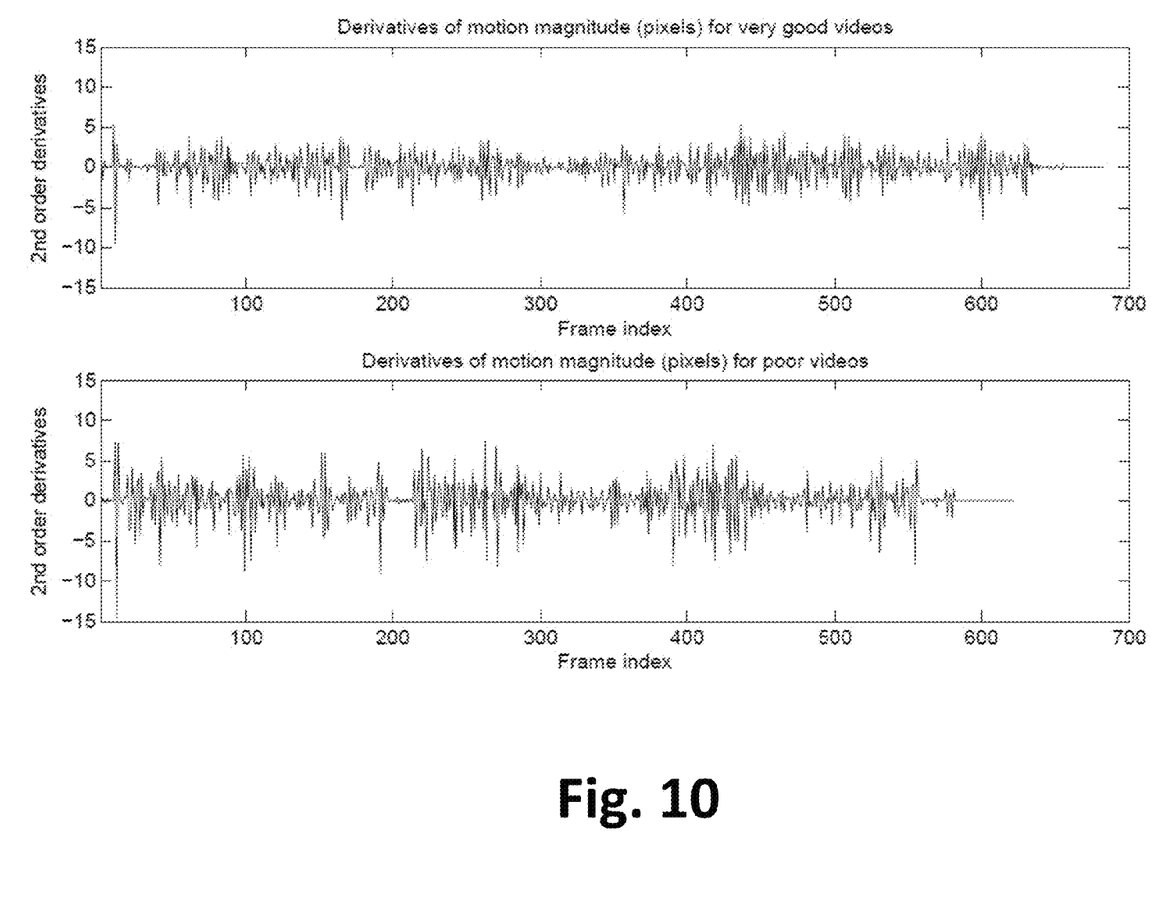
FIG. 10 depicts second order derivatives of optical flow magnitude over very good and poor motion performance image sequence.

For each capsulorrhexis procedure, we compute the motion magnitude for all frames. The range and variance of motion magnitude are used as two motion features. Next, we compute the second order derivative of the motion magnitude curve, as shown in FIG. 10. The values in the second order derivative curve indicate the stability of the motions. Values close to zero indicate stable motions, while larger values correspond to big changes in the optical flow magnitude. Therefore, we use the average value in the second order derivative curve as the third motion feature. Through training a SVM model as shown in Equation (3), we assign the motion score from poor, fair, good to very good.

$$\arg\min_{w,b} \ 0.5 \|w\|^2 \qquad (3)$$
$$\text{S.t.} \ y(w^T X + b) \geq 1$$

Experiments

Dataset

Our dataset comprises 23 videos performed by 5 ophthalmologists. Among them, 3 videos contain multiple capsulorrhexis procedures and the other 20 videos contain only one capsulorrhexis procedure. Therefore, procedure segmentation is not applied to those 20 videos whose key frames and time duration score can be obtained directly from the video. The details of the data set are described in Table 1. For further analysis on cross-validation, we separate our dataset into 4 groups, as indicated in Table 1. Although the video Brooke1 and Brooke2 are performed by the same ophthalmologist, the simulation tools' appearances in the videos are different. Consequently, we separate them into 2 different groups. In further cross-validation analysis, we always train on 3 groups and test on the other group.

TABLE 1

Description of dataset.

| Performer | video name | procedure number | group |
|---|---|---|---|
| Alex | Alex1 | 5 | 1 |
| Seth | Seth1-Seth8 | 8 | 1 |
| Brooke | Brooke1 | 13 | 2 |
| Brooke | Brooke2 | 12 | 3 |
| Bill | Bill1-Bill12 | 12 | 4 |

Evaluation on Duration Score

We select the 3 videos containing multiple capsulorrhexis procedures with the manually labeled starting points and ending points. We compare this ground truth with the results automatically computed by our system in terms of duration difference and key frame difference. Table 2 shows the results of procedure segmentation by comparing the starting time and end time (key frame) of each capsulorrhexis procedure in minutes:seconds format. The error is limited within 2 seconds, which is quite accurate for obtaining the duration score.

TABLE 2

Results for procedure segmentation.

|  | Video 1 | | Video 2 | | Video 3 | |
| --- | --- | --- | --- | --- | --- | --- |
| Point | Actual | Est | Actual | Est | Actual | Est |
| seg 1 | 00:59 | 00:59 | 01:41 | 01:41 | 01:17 | 01:17 |
| seg 2 | 01:09 | 01:08 | 01:56 | 01:56 | 01:30 | 01:29 |
| seg 3 | 02:38 | 02:38 | 03:08 | 03:08 | 02:42 | 02:42 |
| seg 4 | 02:49 | 02:47 | 03:19 | 03:16 | 02:55 | 02:55 |
| seg 5 | 04:11 | 04:11 | 04:44 | 04:45 | 04:07 | 04:07 |
| seg 6 | 04:22 | 04:22 | 04:53 | 04:53 | 04:20 | 04:20 |
| seg 7 | 05:33 | 05:33 | 06:02 | 06:03 | 05:37 | 05:37 |
| seg 8 | 06:06 | 06:05 | 06:10 | 06:10 | 05:55 | 05:55 |
| seg 9 | 07:13 | 07:13 | 07:44 | 07:44 | 07:14 | 07:14 |
| seg 10 | — | — | 08:05 | 08:05 | 07:25 | 07:25 |
| seg 11 | — | — | 09:17 | 09:17 | 08:43 | 08:44 |
| seg 12 | — | — | 09:26 | 09:27 | 08:55 | 08:55 |
| seg 13 | — | — | 10:35 | 10:35 | 10:12 | 10:12 |
| seg 14 | — | — | 10:43 | 10:43 | 10:23 | 10:23 |
| seg 15 | — | — | 12:21 | 12:21 | 11:28 | 11:28 |
| seg 16 | — | — | 12:37 | 12:36 | 11:42 | 11:42 |
| seg 17 | — | — | 14:19 | 14:19 | 12:42 | 12:44 |
| seg 18 | — | — | 14:29 | 14:29 | 12:56 | 12:56 |
| seg 19 | — | — | 15:46 | 15:46 | 14:17 | 17:13 |
| seg 20 | — | — | 16:08 | 16:08 | 14:25 | 14:25 |
| seg 21 | — | — | 17:33 | 17:33 | 15:25 | 15:25 |
| seg 22 | — | — | 17:47 | 17:47 | 15:34 | 15:33 |
| seg 23 | — | — | 19:13 | 19:13 | 16:30 | 16:30 |
| seg 24 | — | — | 19:24 | 19:23 | — | — |
| seg 25 | — | — | 20:34 | 20:34 | — | — |

Evaluation on Spatiality Score

One expert from Flaum Eye Institute graded the 50 capsulorrhexis procedures on the spatiality aspect. The estimated scores and the expert's scores should be as close as possible. However, sometimes the scores assigned by the ophthalmologists are subjective, resulting in the differences even between the experts. As shown in Table 3, circularity is difficult to articulate a standard criterion; therefore we achieve relatively low agreement. Size is a more objective measure and the agreement is the highest among the three sub-factors. Actually, when the expert graded the videos after two months of the first grading, he changed his mind on 40% of the cases where his grading was different from that of the computerized algorithm and agreed with the computer assigned scores. This highlights the issue of subjectivity and supports the consistency of the algorithm.

TABLE 3

Average results of 4-fold cross-validation on grading

|  | |Expert − Computer| | | | |
| --- | --- | --- | --- | --- |
| Sub-Aspect | diff = 0 | diff = 1 | diff = 2 | Accuracy |
| Size | 28 | 12 | 10 | 80% |
| centrality | 20 | 19 | 11 | 78% |
| circularity | 16 | 14 | 20 | 60% |

Evaluation on Motion Score

The same expert and another expert from the same institute graded the 50 capsulorrhexis procedures on the motion aspect. The comparison with the experts' grading in motion scores is shown in Table 4. The "hard" accuracy considers the results correct only if the grades are the same, while the "soft" accuracy considers the results correct when the grades are the same or adjacent. Under hard criterion, our system can achieve the average accuracy of 47%. But we notice that the accuracies of the poor and very good categories are relatively higher than the other two categories, indicating that our system can achieve better performance for extreme conditions. Generally speaking, our system can separate good/very good and fair/poor very well, which is probably more meaningful for the purpose of grading trainees. Actually, even the experts cannot tell the boundary line between good and very good since motion is a very subjective assessment. According to the result, the average soft accuracy reaches 82%, proving the feasibility of our system.

TABLE 4

Motion score comparison with two experts.

|  |  | Computer Score | | | | accuracy | |
| --- | --- | --- | --- | --- | --- | --- | --- |
|  | expert | poor | fair | good | v.g. | strict | broad |
| expert 1 | poor | 3 | 0 | 1 | 0 | 75% | 75% |
|  | fair | 1 | 3 | 2 | 1 | 56% | 89% |
|  | good | 2 | 3 | 6 | 5 | 38% | 88% |
|  | v.g. | 1 | 5 | 4 | 11 | 52% | 71% |
| expert 2 | poor | 2 | 0 | 0 | 0 | 100% | 100% |
|  | fair | 1 | 7 | 3 | 2 | 54% | 85% |
|  | good | 4 | 5 | 7 | 8 | 38% | 88% |
|  | v.g. | 0 | 1 | 8 | 6 | 60% | 90% | v.g. indicates "very good".

Cohen's kappa coefficient is widely used to measure the inter-rater agreement. Larger Cohen's kappa coefficient indicates better agreement between two raters. The definition of Cohen's kappa coefficient k is:

$$k = \frac{Pr(a) - Pr(e)}{1 - pr(e)} \quad (4)$$

In Equation 4, Pr(a) represents the percentage of agreement between two raters, or the percentage of capsulorrhexis procedures with the same gradings between two raters in our case. Pr(e) is the hypothetical probability of agreement between two raters. Cohen's kappa coefficients between computer and two experts are shown in Table 5. Cohen's kappa coefficient between the two experts is 0.260. However, Cohen's kappa coefficients between our system and the two experts are 0.302 and 0.242, respectively, indicating that our system is more consistent and objective.

TABLE 5

Cohen's kappa coefficient of motion scores.

| Performer | computer | expert 1 | expert 2 |
| --- | --- | --- | --- |
| computer | 1 | 0.302 | 0.242 |
| expert 1 | 0.302 | 1 | 0.260 |
| expert 2 | 0.242 | 0.260 | 1 |

To validate our early assumptions about the duration, spatiality and the duration scores, we compute the correlations among the three scores. Results show that the correlation between spatiality and motion is 0.34. The spatiality score can be considered more objective and it is positively correlated with motion score, suggesting that stable motion tends to result in better spatial features. Moreover, the correlation between the motion score and the duration score is −0.41, indicating that unstable motion often leads to longer surgical duration. This is also intuitive because if the surgery performer is not sophisticated and always shakes a lot during the surgery, he tends to have significant hand shake during the surgery and takes a longer amount of time to complete the surgery.

It is, therefore, apparent that there has been provided, in accordance with the various objects of the present invention, a computer vision based method and system for evaluating and grading surgical procedures.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. A computer-based method for evaluating cataract surgical procedures by medical personnel, the method comprising the steps of:
    providing surgical procedure video data on a computer having a processor, memory and computer readable media and storing said surgical procedure video data on the computer readable media;
    identifying with a transform stored on the computer readable media a pupil area of an eye in the surgical procedure video data;
    segmenting the surgical procedure video data based on changes in the pupil area location;
    identifying in the surgical procedure video data each segment as an independent surgical procedure;
    determining time duration of each independent surgical procedure by the time duration of each segment;
    assigning a time duration value to the each independent surgical procedure;
    identifying with the transform stored on the computer readable media key images that indicate completion of a capsulorrhexis procedure;
    within the identified key images, measuring spatial features of a hole made in an anterior capsule of a cataract of the eye or simulated eye during capsulorrhexis;
    assigning a value to the measured spatial features of the hole;
    applying optical flow and resulting optical flow values to compute motion during the capsulorrhexis procedure;
    calculating a stability of the surgical procedure from the computed motion;
    assigning a value to the calculated stability of the surgical procedure; and
    outputting said assigned values for evaluation of the surgical procedure.

2. The computer-based method of claim 1, further comprising the step of assessing performance of a medical person responsible for the surgical procedure using the assigned values.

3. The computer-based method of claim 1, wherein the transform used to identify a pupil area in the surgical procedure video data is a circular Hough transform.

4. The computer-based method of claim 1, further comprising the steps of:
    identifying on the computer action frames where the medical person is performing actions on the pupil;
    identifying on the computer downtime frames in which the medical person is not performing actions on the pupil; and
    retaining on the computer the action frames while discarding the downtime frames.

5. The computer-based method of claim 1, further comprising the step of using Gaussian Mixture Model (GMM) color filtering to remove spurious optical flow values.

6. The computer-based method of claim 2, wherein the step of assessing performance of a medical person responsible for the surgical procedure using the assigned values uses linear regression.

7. The computer-based method of claim 2, wherein the step of assessing performance of a medical person responsible for the surgical procedure using the assigned values uses Support Vector Machine (SVM).

8. The computer-based method of claim 1, wherein the measured spatial feature of the hole made in the anterior capsule of a cataract of an eye or simulated eye during capsulorrhexis is selected from the group consisting of size, circularity and centrality.

9. The computer-based method of claim 1, further comprising the step of correcting for reflected light in the pupil area of the eye as captured in the surgical procedure video data by computer vision inpainting of the reflected light in the pupil area of the eye as captured in the surgical procedure video data.

10. The computer-based method of claim 1, further comprising the step of applying a Gaussian Mixture Model (GMM) to identify effective motion regions for applying optical flow.

11. A computer-based system for evaluating cataract surgical procedures, the system comprising:
    a computer having a processor, memory, and access to computer readable media; the computer configured to receive surgical procedure video data and output performance data of a medical person responsible for the surgical procedure;
    a computer program stored on computer readable media where the computer program executes the steps of:
    identifying with a transform stored on computer readable media a pupil area of an eye in the surgical procedure video data;
    segmenting the surgical procedure video data based on changes in the pupil area location;
    identifying in the surgical procedure video data each segment as an independent surgical procedure;
    determining time duration of each independent surgical procedure by the time duration of each segment;
    assigning a time duration value to the each independent surgical procedure;
    identifying with the transform stored on the computer readable media key images that indicate completion of a capsulorrhexis procedure;
    within the identified key images, measuring spatial features of a hole made in an anterior capsule of a cataract of an eye or simulated eye during capsulorrhexis;
    assigning a value to the measured spatial features of the hole;
    applying optical flow and resulting optical flow values to compute motion during the capsulorrhexis procedure;
    calculating a stability of the surgical procedure from the computed motion;
    assigning a value to the calculated stability of the surgical procedure; and
    outputting said assigned values for evaluation of the surgical procedure.

12. The computer-based system of claim 11, wherein the computer program further comprises the step of assessing performance of a medical person responsible for the surgical procedure using the assigned values.

13. The computer-based system of claim 11, wherein the transform used to identify a pupil area in the surgical procedure video data is a circular Hough transform.

14. The computer-based system of claim 11, wherein the computer program further comprises the steps of:
- identifying on the computer action frames where the medical person is performing actions on the pupil;
- identifying on the computer downtime frames in which the medical person is not performing actions on the pupil; and
- retaining on the computer the action frames while discarding the downtime frames.

15. The computer-based system of claim 11, wherein the computer program further comprises the step of using Gaussian Mixture Model (GMM) color filtering to remove spurious optical flow values.

16. The computer-based system of claim 12, wherein the step of assessing performance of a medical person responsible for the surgical procedure using the assigned values uses linear regression.

17. The computer-based system of claim 12, wherein the step of assessing performance of a medical person responsible for the surgical procedure using the assigned values uses Support Vector Machine (SVM).

18. The computer-based system of claim 11, wherein the measured spatial feature of the hole made in the anterior capsule of a cataract of an eye or simulated eye during capsulorrhexis is selected from the group consisting of size, circularity and centrality.

19. The computer-based system of claim 11, wherein the computer program further comprises the step of correcting for reflected light in the pupil area of the eye as captured in the surgical procedure video data by computer vision inpainting of the reflected light in the pupil area of the eye as captured in the surgical procedure video data.

20. A computer-based method for evaluating surgical procedures by medical personnel, the method comprising the steps of:
- providing surgical procedure video data on a computer having a processor, memory and computer readable media and storing said surgical procedure video data on the computer readable media;
- identifying with a transform stored on computer readable media a region of interest in the surgical procedure video data;
- segmenting the surgical procedure video data based on changes in the region of interest location;
- identifying in the surgical procedure video data each segment as an independent surgical procedure;
- determining time duration of each independent surgical procedure by the time duration of each segment;
- assigning a time duration value to each independent surgical procedure;
- identifying with a transform stored on computer readable media key images that indicate the completion of a specified procedure;
- within the identified key images, measuring spatial features of the region of interest during the surgical procedure;
- assigning a value to the measured spatial features of the region of interest;
- applying optical flow and resulting optical flow values to compute motion during the surgical procedure;
- calculating the stability of the surgical procedure from the computed motion;
- assigning a value to the calculated stability of the surgical procedure; and
- outputting said assigned values for evaluation of the surgical procedure.

* * * * *